United States Patent [19]
Diehl et al.

[11] Patent Number: 5,019,518
[45] Date of Patent: May 28, 1991

[54] PROCESS FOR THE DETECTION OF CHEMICAL WARFARE AGENTS

[75] Inventors: Wolfgang Diehl, Frankfurt; Monika Hepp, Weiterstadt, both of Fed. Rep. of Germany

[73] Assignee: Battelle-Institut e.V., Frankfurt am Main, Fed. Rep. of Germany

[21] Appl. No.: 302,753

[22] Filed: Jan. 27, 1989

[30] Foreign Application Priority Data

Feb. 3, 1988 [DE] Fed. Rep. of Germany ....... 3803142

[51] Int. Cl.$^5$ ............................................. G01N 21/76
[52] U.S. Cl. .................... 436/172; 436/104; 436/106; 436/120; 436/172; 436/800
[58] Field of Search ............... 436/104, 106, 120, 172, 436/800

[56] References Cited

U.S. PATENT DOCUMENTS

4,495,293  1/1985  Shaffar ................................. 436/800
4,599,609  7/1986  Blanchard ......................... 422/55 X

OTHER PUBLICATIONS

*Analytical Chemistry,* vol. 30, No. 7, Jul. 1958, p. 1239.

*Primary Examiner*—Robert J. Warden
*Assistant Examiner*—Stephanie Blythe
*Attorney, Agent, or Firm*—Fisher, Christen & Sabol

[57] ABSTRACT

Process for the detection of a chemical warfare agent, in which a detection reagent able to fluoresce is brought into contact with the chemical warfare agent, which reacts with the chemical warfare agent so that the fluorescent light emitted by the detection agent changes. A detection reagent is used which undergoes this change because of solvent effects. The advantages of the process reside especially in the fact that, not only, as in the prior art, can LOST be detected but now also VX can be detected.

8 Claims, No Drawings

PROCESS FOR THE DETECTION OF CHEMICAL WARFARE AGENTS

BACKGROUND OF THE INVENTION

1. Field Of The Invention

The invention relates to a process for detection of a chemical warfare agent, in which a detection reagent able to fluoresce is brought into contact with the chemical warfare agent, which reacts with the chemical warfare agent so that the fluorescent light emitted by it changes.

2. Background Art

Such a process is described in German OS No. 3,344,700, wherein detection is based on the adduct formation of a triphenylmethine dye with the respective chemical warfare agent. In this case, the detection reagent is explained with a nucleophilic or electrophilic reaction of the chemical warfare agent on a reactive center of the dye or with a conformational change of the dye by adsorptive bonding of the chemical warfare agent on the dye molecule. But only S-LOST (bis(2-chloroethyl) sulfide) and N-LOST (bis(2-chloroethyl)-methylamine hydrochloride) can be detected as chemical warfare agents according to this known process. Detection of the also important chemical warfare agent VX O-ethyl S-(2- diisopropylaminoethyl)methylthiophosphonate alkylthiophosphate) is not possible with the known process.

German PS No. 2,947,459 describes a process for in situ detection of precipitates of special, persistence chemical warfare agents from the group of phosphoric esters. These compounds exhibit a chemiluminescence when indole is used, which can be detected without contact by means of an optical detector. But this reaction does not work for the chemical warfare agent LOST. Addition of silver fluoride a activator is almost always indispensable for detection by means of indole for chemical warfare agent VX. However, some changes can be detected with indole without activator. But the silver fluoride used in this case is expensive and causes problems when used, especially by greatly dispersing samples.

DESCRIPTION OF THE INVENTION

The invention avoids the prior art drawbacks set out above. The object of the invention is to provide a process with which the detection not only of S-LOST and N-LOST but also of VX is effectively done in a simple way.

To achieve this object, the invention is characterized in that a detection reagent is used, which is soluble in a solvent that is not soluble with the chemical warfare agents S-LOST, N-LOST and VX and in that the detection reagent is soluble in the phase of the respective chemical warfare agent so that on contact of the detection reagent with the chemical warfare agent the detection reagent is diffused into the phase of the chemical warfare agent, where it changes the fluorescent light emitted by it. The change of the fluorescent light is thus a change of wavelength or a change of quantum efficiency. Thus, the essence of the invention is that a chemico-physical reagent is used, which has a solubility different from zero in LOST or VX or in the boundary layer between LOST and VX and in the solvent of the detection reagent (generally water), and which in the LOST o VX phase fluoresces at another wavelength or with another quantum efficiency, greatly with a very much higher quantum efficiency, than in the solvent phase (water phase).

Preferably a substance is used as the detection reagent whose fluorescence depends on the position of the acid constant values in the basic state in relation to the acid constant values in the excited state, on the aggregation in the aqueous and in the organic solvent and on the influence of the nonbinding and bonding molecular orbitals by the type of solvent used.

These materials as an aqueous solution in molar concentrations of $10^{-3}$ to $10^{-2}$ are preferably applied to the respective surface on which the chemical warfare agent is suspected of being.

According to the invention, all detection reagents can be used, which are dissolved in the boundary layer of LOST or VX at the phase of the solvent of the detection reagent (water phase) or are concentrated there and which in this boundary layer or in the pure LOST and/or VX phase exhibit a fluorescence property that is changed relative to the solvent phase (water phase). There is no restriction relative to the excitation and emission wavelength. The tested materials cover the total visible light spectrum.

Water and water with an alcohol addition of up to 20 percent are especially suitable as solvents for the detection reagent.

Preferably 6-aminoquinoline or other detection reagents are used, whose logarithm of acid constants in the basic state and their logarithm of the acid constants in the excited state differ by more than two and their protolytic form in an organic solvent fluoresces at a wavelength different from that in water. Also preferably acridine orange, neutral red/light green or other detection reagents are used, whose aggregation properties (dimerization, oligomerization) change with the change from aqueous to organic solvent and their form occurring in organic solvents is able to fluoresce, and their form occurring in $H_2O$ does not fluoresce or fluoresces at another wavelength. Preferably FLUOROL 086, FLURORL 088 (dyes of the BASF company) or another detection reagent is used, whose absorption spectrum and especially fluorescence spectrum shifts in a defined manner with the polarity of the solvent used.

FLUOROL 086 has the formula:

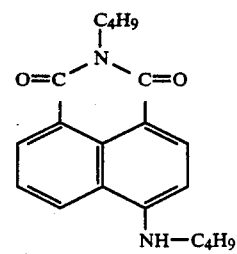

FLUOROL 088 has the formula:

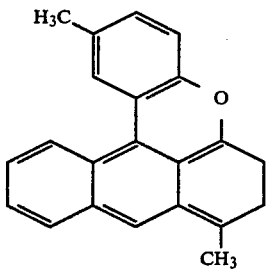

What is claimed is:

1. Process for the detection of a chemical warfare agent, liquid or chemical warfare agent in a liquid comprising providing a detection reagent capable of fluorescing and dissolving in a solvent, chemical warfare agents S-LOST (bis(2-chloroethyl) sulfide), N-LOST (bis(2-chloroethyl)methylamine hydrochloride) and/or VX O-ethyl S-(2-diisoproplyaminoethyl)methylthiophosphonate not being soluble in the solvent, the detection reagent being soluble in the phase of the respective chemical warfare agent and exhibiting in the boundary layer between the phase of S-LOST, N-LOST or VS and the solvent phase or in the pure S-LOST, N-LOST and/or VS phase a fluorescence property different from that in the solvent phase, and contacting said detection agent with a chemical warfare agent so that the detection reagent is diffused into the phase of the chemical warfare agent, where the fluorescent light emitted by the detection reagent in the boundary layer between the phase of the chemical warfare agent and the solvent phase or in the phase of the chemical warfare agent is different form that emitted in the solvent phase.

2. Process according to claim 1 wherein said detection reagent is 6-aminoquinoline.

3. Process according to claim 1 wherein said detection reagent is acridine orange or neutral red/light green.

4. Process according to claim 1 wherein said detection reagent is one of the compounds:

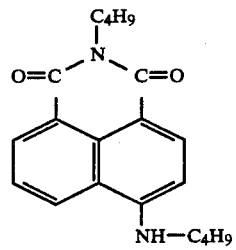 or 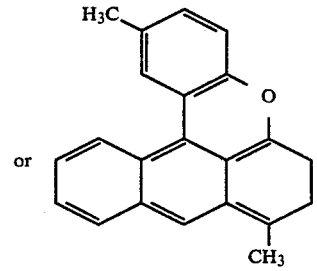

5. Process according to claim 4 wherein said solvent for said detection reagent is a mixture of water with a maximum of 20 percent by weight of an organic solvent.

6. Process according to claim 5 wherein said $1 \times 10^{-3}$ to $1 \times 10^{-2}$ of a molar solution of said detection reagent in said solvent is contacted with said chemical warfare agent.

7. Process according to claim 1 wherein said solvent for said detection reagent is a mixture of water with a maximum of 20 percent by weight of organic solvent.

8. Process according to claim 1 wherein $1 \times 10^{-3}$ to $1 \times 10^{-2}$ of molar solution of said detection reagent said solvent is contacted with said chemical warfare agent.

* * * * *